United States Patent [19]

Han et al.

[11] Patent Number: 4,826,830

[45] Date of Patent: May 2, 1989

[54] TOPICAL APPLICATION OF GLYCIPHOSPHORAMIDE

[76] Inventors: Jui Han, 1 Xian Nong Tan St.; Yan Sun, Cancer Institute & Hospital, 1-4-6, both of Beijing, China

[21] Appl. No.: 761,238

[22] Filed: Jul. 31, 1985

[51] Int. Cl.$^4$ ............................................. A61K 31/66
[52] U.S. Cl. ..................................... 514/118; 514/121
[58] Field of Search ................................ 514/118, 121

[56] References Cited

PUBLICATIONS

Chemical Abstracts 65: 7261g (1966).
The Merck Index, 10th Ed., Merck & Co., Inc., Rahway, N. J., 1983, pp. 475, 1220 and 1221.

*Primary Examiner*—Jerome D. Goldberg
*Attorney, Agent, or Firm*—Jon S. Saxe; George M. Gould; Norman C. Dulak

[57] ABSTRACT

Topical application of glyciphosphoramide for treatment of cancerous ulcerations and tumor conditions are disclosed.

8 Claims, No Drawings

TOPICAL APPLICATION OF GLYCIPHOSPHORAMIDE

The present invention relates to compositions and methods for treating cancerous ulcerations and tumors. More particularly, this invention relates to compositions and methods for treating various types of cancerous ulcers by topically administering glyciphosphoramide to the affected area.

Glyciphosphoramide, N,N-bis(chloroethyl)-N',N''-bis-(carbethoxymethyl)phosphoric triamide, having the structure

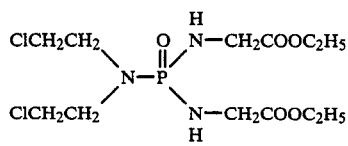

I is a synthetic anticancer agent active against broad tumor spectra in animal tests and has been undergoing evaluation in China for some period of time. Glyciphosphoramide shares the structural moiety of phosphoryl nitrogen mustard with the well known antineoplastic compound Endoxan (cyclophosphamide) which has the structure

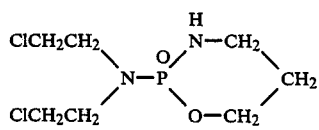

II

Both compounds are devoid of alkylation properties in nonbiological medium at the pH of body fluid as shown by NBP (p-nitrobenzyl-pyridine) test. However, it has been observed that while Endoxan requires prior activation in liver microsome to be effective, glyciphosphoramide is activated in the presence of plasma or serum. This unique property of glyciphosphoramide makes the compound a useful agent for topical use in the treatment of cancerous ulceration and malignant tumor.

In accordance with the invention, a method for treating cancerous ulcerations comprises topically administering to the affected skin area a therapeutically effective amount of glyciphosphoramide. The total dose used in one course of treatment is in the range of 10–20 grams.

The treatment of cancerous ulcerations according to the present invention involves topical application of glyciphosphoramide in preparations, such as neat fine or microcrystalline powder form or in a pharmaceutical composition comprising 1–99% by weight of the active ingredient in an inert, physiologically acceptable carrier. The carrier material should not react with or otherwise reduce the effectiveness of glyciphosphoramide. Suitable physiologically acceptable carriers include: water, alcohols, such as ethanol, propanol and the like, propylene glycol; polyethylene glycol; mineral oil; vegetable oil; petrolatum; silicone materials, dimethylsulfoxide, and the like. Preferred carriers include dimethylsulfoxide and silicone materials. The compositions are preferably prepared in powder, spray, lotion, cream, oil or emulsion formulations for administration in accordance with the present invention.

There may also be incorporated into the compositions employed in the practice of the present invention additional ingredients or pharmaceutical adjuvants recognized in the art of pharmaceutical compounding of topical formulations. Pharmaceutical adjuvants that may be used include stabilizers, such as human serum albumin; preservatives, such a phenol, methyl paraben, propyl paraben; antioxidants, such as butylated hydroxy anisole, butylated hydroxy toluene; and the like. The choice of such materials and the amounts to be utilized are considered to be within the purview of one skilled in the art. It is to be borne in mind, however, that such conventional pharmaceutical adjuncts which might adversely affect the topical compositions employed in the present invention are not suitable for use herein.

The topical compositions employed in the practice of this invention are prepared by conventional techniques well established in the art.

The manner in which the topical compositions are employed will be readily apparent from the foregoing description, as well as from the examples which follow. The glyciphosphoramide containing compositions can be applied in a thin layer with or without an occlusive dressing to the subject to be treated. Application of the composition may be accomplished by use of a cotton swab, soft brush, sponge, by spraying or applied directly from a container. The affected area is treated once or twice daily for a period of about ten (10)–thirty (30) days by topical administration of a pharmaceutical composition containing glyciphosphoramide.

Topical application of glyciphosphoramide is significantly effective in the treatment of cancerous ulceration. However for the stand point of treatment of cancer as a whole, it has also been found more beneficial to combine topical treatment of glyciphosphoramide with oral treatment of glyciphosphoramide or other well known antitumor compounds.

For a fuller understanding of the nature of this invention, reference may be had to the following examples which are given merely as further illustrations of the invention and are not to be construed in a limiting sense.

As used in the Examples, GPM is glyciphosphoramide.

EXAMPLE 1

Inhibition of the Growth of HeLa Cells by GPM in vitro

The HeLa cells were cultivated in Eagle MEM medium supplemented by 10% new born calf serum and penicillin plus streptomycin. Various concentrations of GPM solution were added in experimental flasks and 24 hours, 48 hours and 72 hours after the addition of the drug the number of tumor cells was counted. In addition a series of smears were made and the morphological features were studied.

Results demonstrated that at a concentration of $2.5 \times 10^{-4}$M GPM exhibited a significant inhibition of the cell growth and the mitotic index was decreased signficantly. In contrast to GPM, a concentration of $1 \times 10^{-3}$M of Endoxan had no effect on the cell growth. Morphological studies showed that under the action of GPM the size of HeLa cells was enlarged and the cells showed a peculiar shape with several thin filaments similar to astrocytes.

EXAMPLE 2

Studies on the Local Application of GPM on Rats bearing Transplantable Tumors In view of the fact that dimethylsulfoxide (DMSO) promotes the penetration of drugs through the skin, a series of experiments were undertaken in rats. GPM was dissolved in DMSO as 1-2% solution and painted for 8-10 times upon the shaved skin which covered the solid tumor (Walker carcinoma 256 or Jensen sarcoma) in rats.

Results disclosed that three days after the transplantation of Walker carcinoma 256 or Jensen sarcoma cells the painting of GPM-DMSO solution on shaved skin of tumor bearing rats resulted in a significant inhibition of tumor growth (Table 1). When the Walker carcinoma 256 cells were transplanted in both sides of the trunk of rats the topical application of GPM-DMSO solution on one side of the skin caused a same degree of inhibition of tumor growth in both side (Table 1).

TABLE 1

Therapeutic Effect of Topical Application of GPM on Walker Carcinoma 256 bearing Rats

| Tumor Type | Group | No. of Animals initial | No. of Animals final | Body weight (g) initial | Body weight (g) final | Tumor Wt. (g) | | Tumor inhibitory rate (%) | |
|---|---|---|---|---|---|---|---|---|---|
| Walker Carcinoma 256 | Control | 10 | 10 | 63 | 94 | 6.1 | | | |
| | 2% GPM | 10 | 10 | 66 | 76 | 1.7 | | 72 | |
| | | | | | | Left | Right | Left | Right |
| | Control* | 13 | 13 | 67 | 87 | 3.9 | 3.1 | | |
| | 2% GPM | 10 | 10 | 67 | 90 | 0.97 | 0.63 | 75 | 80 |
| Jenson Sarcoma | Control | 10 | 10 | 66 | 105 | 5.6 | | | |
| | 2% GPM | 10 | 10 | 65 | 101 | 0.2 | | 96 | |

*Tumor cells were transplanted in both side of the trunk of rats.

TABLE 2

Clinical Results of Topical and combinaion of Topical and Oral application of GPM in the treatment of Cancerous Ulceration

| Kind of cancer | No. of cases Total | No. of cases Topical | No. of cases Combination | Effective Rate % |
|---|---|---|---|---|
| Cervical cancer* | 26 | 26 | | 88.4 |
| Breast cancer | 30 | 19 | 11 | 96.7 |
| Malignant lymphoma | 3 | 2 | 1 | all positive |
| Squamous cancer | 2 | 1+ | 1 | one positive |
| Adenocarcinoma (pancreas, ulceration in metastatic lymphonodus) | 1 | | 1 | positive |
| Skin cancer | 1 | | | positive |

*Including nonulcerated cancer

EXAMPLE 4

In one clinical study 20% glyciphosphoramide in dimethylsulfoxide solution or powder preparation was sprayed or smeared at the site of ulceration twice a day.

EXAMPLE 3

Based upon the pharmacological results, the topical application of GPM was introduced to clinical trails. GPM was used in preparations, as neat, fine or microcrystalline powder form, 20% of DMSO solution, 20-30% in silicon cream and other types ointments. Table 2 summarized the clinical results of 63 cases of topical use of GPM alone or combined with oral administration of GMP in the treatment of cancerous ulceration. Flattening and reducing the area of ulcer and in some cases complete healing were observed after treatment. At the same time it decreased the effusion or stopped the effusion from the ulcer and it also relieved the unbearable cancerous pain and odor. Histological change of cancer cells, proliferation of connective tissue and frequently shrinkage of the size of cancer were also the results of treatment. No noticeable toxic effect was observed except in very few cases showing irritation because of the impure DMSO used. In the 30 cases of ulcerated advanced breast cancer, 19 patients were treated with GPM topically alone for judging the efficacy of this special route of administration. Combination of topical and oral GPM were used in 9 cases and in the rest two cases local GPM were given along with oral administration of other anticancer agents. Cancerous ulceration are cases stubborn to treat. The positive results of 29 out 30 cases of breast cancerous ulceration thus treated either by topical or topical combining with oral were most significant.

One course of treatment lasted from 10 to 20 days.

Criteria for determining efficacy included 4 categories: complete remission (CR), partial remission (PR), stable (S), and progressive (P) [3]. The efficacy rate was calculated according to the following formula: (CR+PR)/total number of cases×100%.

The therapeutic efficacy could be analyzed statistically in 42 patients (Table 3). The numbers of patients with adenocarcinoma of the breast and carcinoma of the uterine cervix were relatively large. Other cancers included malignant lymphoma, etc. Fifteen out sixteen patients with ulceration of adenocarcinoma of the breast treated at the Chinese Academy of Medical Sciences Cancer Hospital showed definite drug effects. The size of the tumor was reduced. The ulceration became flat or healed. The histological examination revealed degeneration of cancer cells and hyperplasia of the connective tissue. One patient received unsuccessful surgical treatment and radiation treatment of breast cancer and had a large ulceration at the chest. The patient received local application of the test drug and systemic administration of low doses of other drugs occasionally. Cancer cells became undetectable in the excreta and biopsy specimens, and the wound healed. This patient has resumed her normal work for 20 years. 6 of 9 patients with carcinoma of the uterine cervix treated in the hospital mentioned above showed the therapeutic efficacy. Of 15 cases of carcinoma of the uterine cervix treated at the Hospital of Chinese Traditional Medicine in Beijing 3 cases showed a remarkable decrease in the size of the tumor, 11 cases showed a decrease in the size of the tumor, and the drug was not effective in one case. In some patients, the drug treatment resulted in the disappearance of the cancer cells and the histological examination revealed degenerative changes, remarkable hyperplasia of the connective tissue, and scar formation.

TABLE 3

| | Clinical Efficacy of GPM Administered Topically | | | | | |
|---|---|---|---|---|---|---|
| Disease Type | Number of cases | CR | PR | S | P | Efficacy rate % |
| Adenocarcinoma of the breast | 16 | 3 | 12 | 1 | | 93.8 |
| Carcinoma of the uterine cervix | 24* | | 20 | 4 | | 83.3 |
| Malignant lymphoma | 2 | | 2 | | | 100 |
| Total | 42 | 3 | 34 | 5 | | |

*Including nonulcerated carcinoma

We claim:

1. A method for treating cancerous ulcerations and tumors comprising topical administration to an animal or human being having a cancerous ulceration or tumor selected from the group consisting of squamous cancer, malignant lymphoma, carcinoma of the uterine cervix and adenocarcinoma of the breast, which cancerous ulceration or tumor is susceptible to topical administration, of an amount of glyciphosphoramide that is effective for topical treatment of such cancerous ulcerations and tumors.

2. The method of claim 1 wherein the total dose used in one course of treatment is from about 10–20 grams.

3. The method of claim 2 wherein the neat fine or microcrystalline glyciphosphoramide is topically administered.

4. The method of claim 2 wherein the glyciphosphoramide is topically administered in the form of a pharmaceutical composition comprising from about 1 to 99% by weight of the active ingredient and the remainder of the composition being an inert physiologically acceptable carrier material.

5. The method of claim 4 wherein the carrier material is dimethylsulfoxide.

6. The method of claim 4 where the carrier material is physiologically inert silicone material.

7. A pharmaceutical composition for topical treatment of cancerous ulcerations and tumors comprising an amount of glyciphosphoramide that is effective for topical treatment of cancerous ulcerations and tumors selected from the group consisting of squamous cancer, malignant lymphoma, carcinoma of the uterine cervix and adenocarcinoma of the breast, which cancerous ulcerations and tumors are susceptible to topical treatment, either alone as a neat, fine or microcrystalline powder or in combination with an inert physiologically acceptable carrier material selected from the group consisting of water, ethanol, propanol, propylene glycol, polyethyleneglycol, mineral oil, vegetable oil, petrolatum, silicone materials and dimethylsulfoxide.

8. The pharmaceutical composition of claim 7 wherein the glyciphosphoramide is present in an amount of from 1–99% by weight of the composition.

* * * * *